Figure 1:
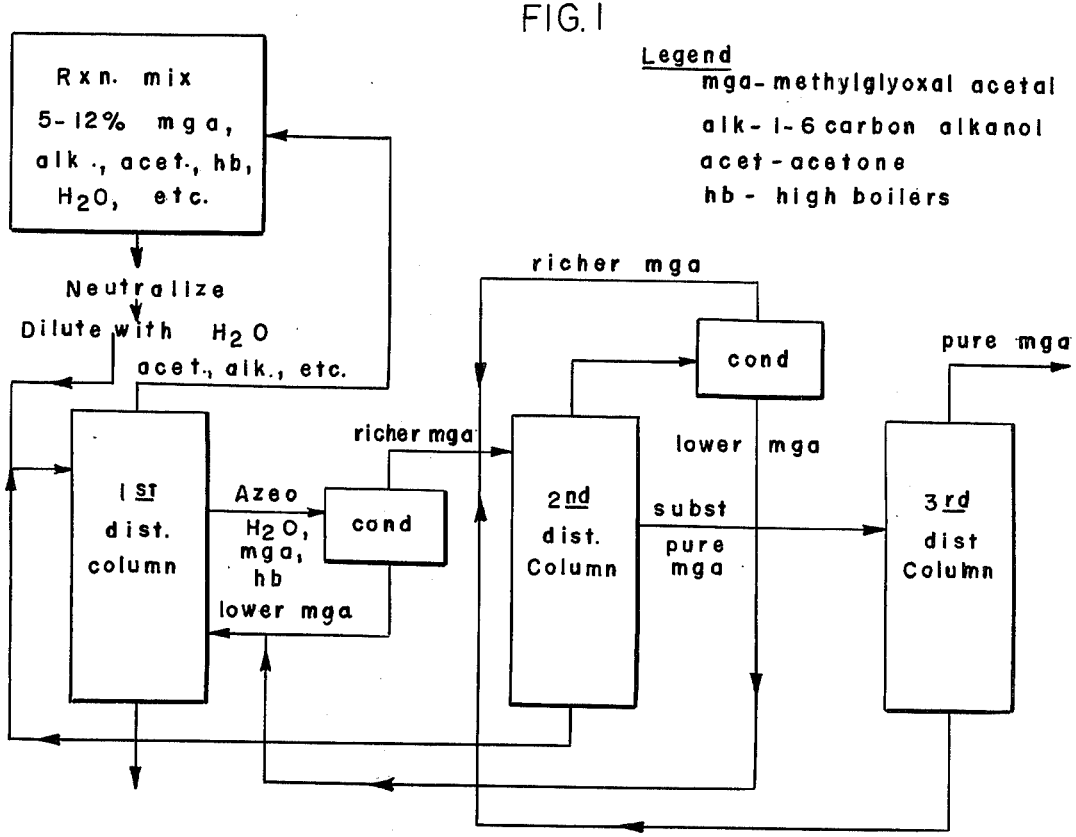

United States Patent [19]

Bittler

[11] 3,956,074

[45] May 11, 1976

[54] RECOVERY OF METHYLGLYOXAL ACETAL BY PLURAL STAGE DISTILLATION WITH INTERMEDIATE PHASE SEPARATION

[75] Inventor: Knut Bittler, Ludwigshafen, Germany

[73] Assignee: BASF Aktiengesellschaft, Ludwigshafen (Rhine), Germany

[22] Filed: July 10, 1974

[21] Appl. No.: 487,235

[30] Foreign Application Priority Data

July 31, 1973  Germany............................ 2338665

[52] U.S. Cl..................................... 203/76; 203/77; 203/78; 203/79; 260/615 A; 260/615 AA
[51] Int. Cl.$^2$...................... B01D 3/00; B01D 3/10; B01D 3/38
[58] Field of Search......... 260/615 A, 615 AA, 616, 260/614 R, 615 R; 203/76, 79, 83, 85, 92, 95, 71–75, 77, 80–82, 84, 91, 93, 94, 96–98

[56] References Cited
UNITED STATES PATENTS 2,588,272   3/1952   Morrell et al.......................... 203/83

FOREIGN PATENTS OR APPLICATIONS 1,252,193   10/1967   Germany........................ 260/615 A

*Primary Examiner*—Norman Yudkoff
*Assistant Examiner*—Frank Sever
*Attorney, Agent, or Firm*—Johnston, Keil, Thompson & Shurtleff

[57]  ABSTRACT

A process for the recovery of methylglyoxal acetal from a reaction mixture which has been obtained in the reaction of acetone with an alcohol and a nitrosation agent or oxidizing agent in the presence of an acid catalyst followed by neutralization which comprises diluting the neutralized reaction mixture with such an amount of water that a homogeneous solution is formed, subsequent distillation in a first column in which a mixture of acetone, alcohol and solvent is removed overhead and returned direct to the synthesis and an azeotrope of methylglyoxal acetal, water and high-boilers is withdrawn as a side stream, condensation of the azeotrope thus obtained and separation of the phase rich in methylglyoxal acetal, subsequent distillation of the phase rich in methylglyoxal acetal thus obtained in a second column in which purified methylglyoxal acetal is withdrawn as a side stream and the overhead and bottoms products are returned with the feed to the first column, pure methylglyoxal acetal being obtained as the overhead product in a third column. Methylglyoxal acetal is suitable for the production of animal feed supplements.

12 Claims, 2 Drawing Figures

RECOVERY OF METHYLGLYOXAL ACETAL BY PLURAL STAGE DISTILLATION WITH INTERMEDIATE PHASE SEPARATION

This application discloses and claims subject matter described in German Pat. No. P 23,38,665.4, filed July 31, 1973, which is incorporated herein by reference.

The invention relates to a process for the recovery of methylglyoxal acetal from a reaction mixture which has been obtained in the reaction of acetone with an alcohol and a nitrosation agent in the presence of an acid catalyst followed by neutralization.

It is known from German Pat. No. 1,252,193 that solutions containing methylglyoxal acetal are obtained by reaction of acetone with an alcohol and a nitrosation agent in the presence of an acid catalyst. The solution thus obtained is then neutralized. Excess acetone and excess alcohol are distilled off from the mixture obtained. The aqueous solution which remains is diluted with water and methylglyoxal acetal is extracted with a solvent which is not soluble in water and then methylglyoxal acetal is recovered from the extract by distillation. To make the process economical and to increase the yield of methylglyoxal acetal it is necessary to hydrolyze the 1,1,2,2-tetraalkoxypropane obtained as a byproduct with sulfuric acid and to recover therefrom additional methylglyoxal acetal. Moreover it is necessary to purify the recovered starting material and the solvent separately. Such operations are very expensive industrially.

It is an object of the invention to provide a process in which fewer purification steps than hitherto are necessary for the recovery of methylglyoxal acetal from solutions containing the same. Another object of the invention is to provide a process in which separate processing of the 1,1,2,2-tetraalkoxypropanes formed as byproducts is dispensed with.

In accordance with this invention these and other objects and advantages are achieved in a process for the recovery of methylglyoxal acetal from a reaction mixture which has been obtained in the reaction of acetone with an alcohol and a nitrosating agent or oxidizing agent in the presence of an acid catalyst followed by neutralization, which comprises diluting the neutralized reaction mixture with such an amount of water that a homogeneous solution is formed, distilling the reaction mixture in a first column where a mixture of acetone, alcohol and solvent is distilled off overhead and returned direct to the synthesis and an azeotrope of methylglyoxal acetal, water and high-boilers is withdrawn as a side stream, condensing this azeotrope, separating therefrom the phase richer in methylglyoxal acetal which is distilled in a second column where purified methylglyoxal acetal is withdrawn as a side stream and the overhead and bottoms products are returned to the feed into the first column and recovering pure methylglyoxal acetal as the overhead product in a third column.

Solutions containing methylglyoxal acetal may be obtained for example by the method described in German Pat. No. 1,252,193. Pure acetone or technical acetone may be used as starting material. Suitable alcohols generally contain one to twenty carbon atoms. It is particularly preferred to use alkanols or alkanediols of up to six carbon atoms and preferably up to two carbon atoms.

The nitrosating agent or oxidizing agent used may be nitrous acid or a compound which is easily converted into nitrous acid under the reaction conditions such as dinitrogen trioxide or an alkyl nitrite.

Strong inorganic acids and Lewis acids such as hydrogen chloride, aluminum chloride, zinc chloride or iron(III) chloride are suitable acid catalysts.

For each mole of acetone there are generally used from 1 to 20 moles and particularly from 3 to 5 moles of alcohol and from 0.5 to 2.5 moles and particularly from 1.0 to 2.0 moles of nitrosation agent. The acid catalysts are used as a rule in an amount of from 1 to 10% by weight based on the mixture of reactants. The reaction is advantageously carried out with the additional use of a solvent such as methyl acetate, methylal, methylene chloride or an aromatic hydrocarbon such as benzene or toluene. The temperature maintained is generally from 0° to 150°C and particularly from 20° to 80°C.

The reaction mixture is neutralized after the reaction is over. An aqueous caustic alkali solution, for example caustic soda solution or caustic potash solution of a concentration of from 10 to 30% by weight is generally used for the purpose. The reaction mixture advantageously has a pH of from 7 to 9 after neutralization. Typical reaction mixtures contain for example from 5 to 15% by weight of acetone, from 5 to 12% by weight of methylglyoxal acetal, from 15 to 35% by weight of alcohol, from 15 to 30% by weight of solvent, from 10 to 15% by weight of water, from 2 to 6% by weight of alkali salts and from 5 to 10% by weight of high-boilers. A typical mixture contains for example 10.6% by weight of acetone, 9.8% by weight of methylglyoxal dimethylacetal, 29.8% by weight of methanol, 24.3% by weight of a mixture of methyl acetate and methylal, 13.1% by weight of water, 4.3% by weight of sodium salts and 8.1% by weight of high-boilers.

The reaction mixture thus obtained is diluted with such an amount of water that a homogeneous solution is formed, i.e. until all solid substances have dissolved. The amount of water generally depends on the amount of salts contained in the reaction mixture. These have to be brought completely into solution. The necessary amount for a given reaction mixture may be established immediately by a simple test.

The solution thus obtained is distilled in a first column. Examples of suitable columns are packed columns and bubble tray columns. Suitable columns advantageously have from 10 to 30 and particularly from 22 to 24 theoretical trays. The starting mixture is conveniently fed in within the upper one-third of the column. A mixture of acetone, alcohol and solvent is distilled off overhead while a side stream of an azeotrope of methylglyoxal acetal, water and high-boilers is withdrawn advantageously five to seven trays below the feed of the starting solution. Excess water in which dissolved alkali metal salts and organic byproducts are present is drawn off at the bottom. It has proved to be convenient to supply steam as a direct heat carrier into the foot of the column (below the first theoretical tray).

The azeotrope of methylglyoxal acetal, water and high-boilers obtained as a side stream is condensed, separated into two phases of which the lower is returned to the first column and the upper phase is advantageously distilled in a second column at subatmospheric pressure. The mixture is advantageously supplied to the second column in the upper one-third of the same. The second column conveniently has five to fifteen and particularly from ten to twelve theoretical trays. The product obtained overhead in the second column is similarly the azeotrope of methylglyoxal acetal and water which is condensed and which forms two phases of which the upper phase is returned to the column and the lower phase is conveniently returned to the first column, while high-boilers are withdrawn as bottoms product and returned with the feed to the first column. Purified methylglyoxal acetal is removed as a side stream in the middle of the column conveniently six to seven theoretical trays above the bottoms; it is purified in a third column advantageously having five to six theoretical trays from which pure methylglyoxal acetal is recovered as the overhead product.

The overhead product obtained in the first column and which consists substantially of acetone, alcohol and solvent is returned to the synthesis without further separation.

Methylglyoxal acetal is a sought-after organic intermediate and is used for example in the production of animal feed supplements, for example as an agent for promoting increase in weight in stock raising.

Figure 2:
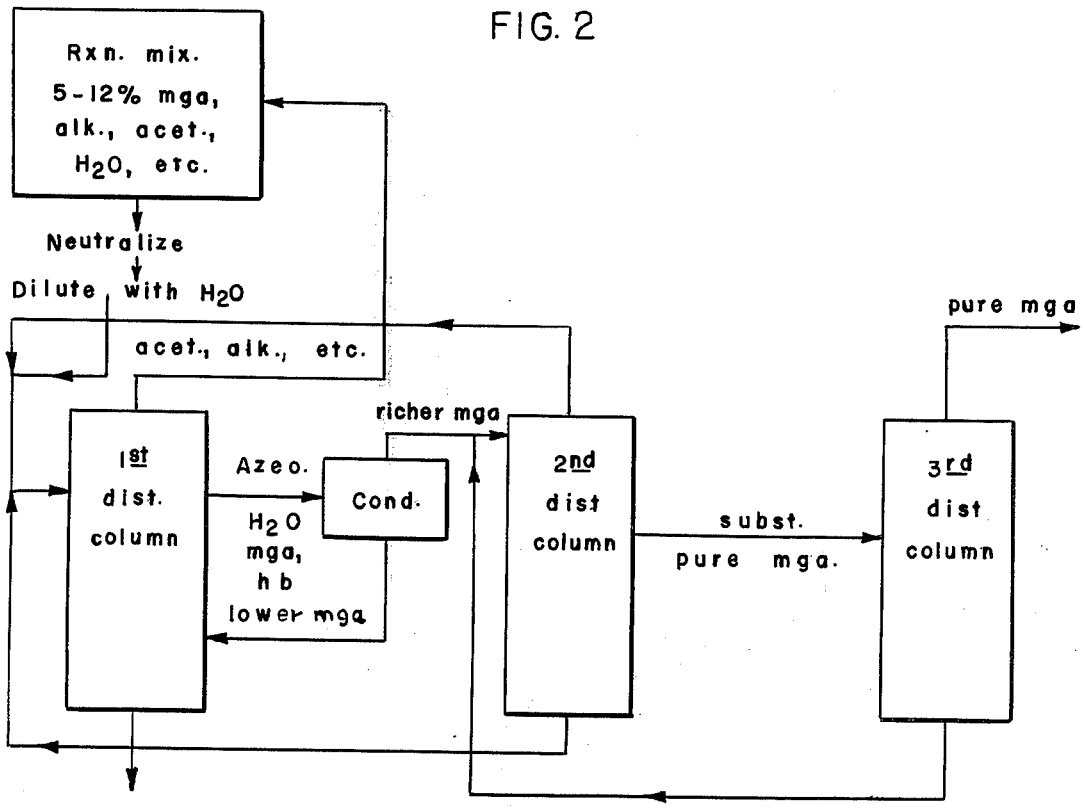

The above described processes are illustrated diagrammatically in the drawing, wherein:

FIG. 1 is a block flow diagram of the process wherein the upper phase of the condensate of the second distillation column's overhead is returned to the second column while the lower phase of the condensate is returned to the first column; and FIG. 2 is a block flow diagram of the process in which both the overhead and bottoms of the second distillation column are returned to the first distillation column.

The process according to the invention will be illustrated in the following Example. Parts given in the Example are parts by weight and they bear the same relation to parts by volume as the kilogram to the liter. Percentages are also by weight.

EXAMPLE 250 parts of water is added to 1356.1 parts per hour of a solution containing methylglyoxal dimethyl acetal which (after neutralization with caustic soda solution) consists of 8.1% of acetone, 8.6% of methylglyoxal dimethyl acetal, 33.0% of methanol, 26.2% of a mixture of methylal and methyl acetate, 11.8% of water, 3.6% of sodium salts and 8.7% of high boiling point byproducts. The solution thus obtained is united with 302.1 parts of returned products and supplied to the 14th tray of a column having 23 theoretical trays. 914 parts per hour of a mixture of acetone, methanol, methyl acetate and methylal is withdrawn at the top of the column while 2139.5 parts mainly of water with salts and byproducts is drained off from the bottoms. In addition 1565.4 parts of steam is supplied per hour to the bottom of the column. A temperature of 59°C is maintained at the top of the column and a temperature of 100°C in the bottoms. At a point six trays below the feed there is removed per hour 420.1 parts of an azeotrope of methylglyoxal dimethyl acetal and water and also high-boilers and this separates into two phases. The upper phase rich in acetal is fed to the top of a second column having twelve theoretical trays. A top temperature of 62°C and a bottoms temperature of 100°C are maintained in the second column at 135 mm. 58 parts per hour are taken overhead (this is mainly water and methylglyoxal dimethylacetal which are returned to the first column) while 46 parts per hour of high-boilers which still contain methylglyoxal dimethyl acetal are withdrawn from the bottoms and returned to the feed to the first column. At the seventh tray there is withdrawn as a side stream 125 parts per hour of purified methylglyoxal dimethyl acetal which is fed to the first tray of a third column having six theoretical trays. A top temperature of 79°C at 115 mm and a bottoms temperature of 86°C are maintained in the third column. 118 parts per hour of methylglyoxal dimethyl acetal which is contaminated with a trivial amount of water and with up to 0.1% of methylglyoxal tetramethyl acetal is obtained overhead. The high-boilers obtained in the bottoms are returned to the second column.

I claim:

1. A process for the recovery of methylglyoxal acetal from a reaction mixture containing 5–12% by weight of methylglyoxal acetal which has been obtained by a synthesis reaction by the oxidation of acetone in the presence of an alkanol having up to six carbon atoms in mixture with an acid catalyst, followed by neutralization of the reaction mixture, which comprises
   a. diluting the neutralized reaction mixture containing 5–12% water to form a homogeneous solution;
   b. distilling the diluted reaction mixture in a first column where a mixture of acetone, and said alkanol is taken overhead and returned to the synthesis stage while an azeotrope of methylglyoxal acetal, water and high-boilers is withdrawn as a side stream, the bottoms being discarded;
   c. condensing said azeotrope;
   d. forming in the condensed azeotrope an upper phase which is richer in methylglyoxal acetal and a lower phase which is lower in methylglyoxal acetal, and returning the lower phase to the first column;
   e. distilling said upper phase in a second column, the bottoms being returned to the first column, the overhead being condensed and separated into an upper phase which is richer in methylglyoxal acetal and which is returned to the second column while the lower phase is returned to the first column, and substantially purified methylglyoxal acetal being withdrawn as a side stream which is
   f. introduced into a third distillation column from which pure methylglyoxal acetal is withdrawn overhead and the bottoms are returned to the second column.

2. A process as claimed in claim 1 wherein the first column has from 10 to 30 theoretical trays.

3. A process as claimed in claim 1 wherein the reaction mixture which has been neutralized and diluted with water is fed into the upper one-third of the first column.

4. A process as claimed in claim 1 wherein an azeotrope of methylglyoxal acetal, water and high-boilers is withdrawn as a side stream from the first column five to seven trays below the point of the feed.

5. A process as claimed in claim 1 wherein methylglyoxal acetal is withdrawn as a side stream at a point in the second column which is from six to seven theoretical trays above the bottoms.

6. A process as claimed in claim 1 wherein said neutralized reaction mixture contains 5 to 15% by weight of acetone, from 5 to 12% by weight of methylglyoxal acetal, from 15 to 35 by weight of said alkanol, from 15 to 30% by weight of solvent, from 10 to 15% by weight of water, from 2 to 6% by weight of alkali metal salts and from 5 to 10% by weight of high-boilers, and said solvent being methylacetate, methylal, methylene chloride, benzene or toluene.

7. A process for the recovery of methylglyoxal acetal from a reaction mixture containing 5–12% by weight of methylglyoxal acetal which has been obtained by a synthesis reaction by the oxidation of acetone in the presence of an alkanol having up to six carbon atoms in mixture with an acid catalyst, followed by neutralization of the reaction mixture, which comprises
  a. diluting the neutralized reaction mixture containing 5-12% by weight of methylglyoxal acetal with sufficient water to form a homogeneous solution;
  b. distilling the diluted reaction mixture in a first column where a mixture of acetone and said alkanol is taken overhead and returned to the synthesis stage while an azeotrope of methylglyoxal acetal, water and high-boilers is withdrawn as a side stream, the bottoms being discarded;
  c. condensing said azeotrope;
  d. forming in the condensed azeotrope an upper phase which is richer in methylglyoxal acetal and a lower phase which is lower in methylglyoxal acetal, and returning the lower phase to the first column;
  e. distilling said upper phase in a second column, both the bottoms and overhead being returned to the first column and substantially purified methylglyoxal acetal being withdrawn as a side stream which is;
  f. introduced into a third distillation column from which pure methylglyoxal acetal is withdrawn overhead and the bottoms are returned to the second column.

8. A process as claimed in claim 7 wherein the first column has from 10 to 30 theoretical trays.

9. A process as claimed in claim 7 wherein the reaction mixture which has been neutralized and diluted with water is fed into the upper one-third of the first column.

10. A process as claimed in claim 7 wherein an azeotrope of methylglyoxal acetal, water and high-boilers is withdrawn as a side stream from the first column five to seven trays below the point of the feed.

11. A process as claimed in claim 7 wherein methylglyoxal acetal is withdrawn as a side stream at a point in the second column which is from six to seven theoretical trays above the bottoms.

12. A process as claimed in claim 7 wherein said neutralized reaction mixture contains 5 to 15% by weight of acetone, from 5 to 12% by weight of methylglyoxal acetal, from 15 to 35% by weight of said alkanol, from 15 to 30% by weight of solvent, from 10 to 15% by weight of water, from 2 to 6% by weight of alkali metal salts and from 5 to 10% by weight of high-boilers, and said solvent being methylacetate, methylal, methylene chloride, benzene or toluene.

* * * * *